United States Patent [19]

Dembicki, Jr. et al.

[11] 4,325,907
[45] Apr. 20, 1982

[54] PYROLYSIS PRODUCT GASES ANALYZING METHOD AND SYSTEM

[75] Inventors: Harry Dembicki, Jr.; Roger A. Woods, both of Ponca City, Okla.

[73] Assignee: Conoco Inc., Ponca City, Okla.

[21] Appl. No.: 189,737

[22] Filed: Sep. 22, 1980

Related U.S. Application Data

[62] Division of Ser. No. 37,938, May 9, 1979, abandoned.

[51] Int. Cl.³ .................... G01N 31/12; G01N 31/06; G01N 31/08; G01N 21/74
[52] U.S. Cl. ................... 422/54; 23/230 PC; 23/232 C; 422/80; 422/89

[58] Field of Search ............... 422/54, 78, 80, 88, 422/89; 23/230 PC, 232 E

[56] References Cited

U.S. PATENT DOCUMENTS 3,545,929 12/1970 Linnenbom et al. ............ 422/54
4,102,648 7/1978 Hartmann et al. ............. 422/54
4,133,640 1/1979 Clinton et al. ................ 422/78

Primary Examiner—Michael S. Marcus
Attorney, Agent, or Firm—William J. Miller

[57] ABSTRACT

An improved method and system for analyzing pyrolysis product gases wherein a portion of the gases are collected while another portion is being analyzed during the pyrolysis reaction.

6 Claims, 2 Drawing Figures

PYROLYSIS PRODUCT GASES ANALYZING METHOD AND SYSTEM

This is a division of application Ser. No. 37,938, filed May 9, 1979, now abandoned.

BACKGROUND OF THE INVENTION

1. Field of the Invention

The present invention relates to improved methods and systems for analyzing pyrolysis product gases, and more particularly, but not by way of limitation, to improved methods and systems for analyzing pyrolysis product gases during the production thereof.

2. Description of the Prior Art

The pyrolysis of a substance into one or more other substances is well known. Pyrolysis involves the application of heat to one or more compounds whereby the compounds decompose or higher molecular weight compounds are formed. Hydrocarbons are commonly subjected to pyrolysis to produce lower molecular weight compounds. For example, the pyrolysis of methane at about 1300° C. brings about the formation of carbon black and hydrogen. The pyrolysis of gaseous alkanes at from about 500° to about 600° C., brings about the decomposition of the alkanes and is commonly referred to as thermal cracking.

In industry, and particularly in the petroleum and chemical industries, it is often desirable and/or necessary to subject compounds or substances to pyrolysis and to determine the particular products and amounts thereof produced thereby. For example, core samples from subterranean earth formations are subjected to pyrolysis and the products produced thereby analyzed to determine the hydrocarbon content of the samples and other information relative to the subterranean earth formation from which the samples were taken. Heretofore, pyrolysis testing has been carried out by placing a compound or substance to be pyrolyzed in a pyrolysis oven and heating the substance in the presence of an inert gas such as helium to a temperature level whereby pyrolysis occurs. The resulting pyrolysis product gases mixed with the inert gas utilized are analyzed using conventional analytical instruments such as a gas chromatograph.

In order to collect and analyze all of the pyrolysis product gases produced, a trap is utilized which retains the gases, such as by condensing and accumulating the condensed gases, after which the condensed gases are revaporized and analyzed. Where the pyrolysis of a substance is carried out under increasing temperature conditions and it is desirable to collect and analyze the product gases produced over different temperature ranges and/or where the pyrolysis is carried out at a constant temperature and it is desirable to collect and analyze portions of the gases produced separately according to time period, the heretofore used procedure requires that the pyrolysis reaction be carried out in two or more steps which is extremely difficult and time consuming.

By the present invention a method and system for collecting and analyzing pyrolysis product gases in two or more portions while carrying out the pyrolysis reaction in a single continuous step are provided. In addition, a portion of the pyrolysis product gases produced during the reaction is analyzed while an additional portion is being collected thereby reducing the overall time required for a full analysis of the gases to be carried out.

SUMMARY OF THE INVENTION

A method of analyzing pyrolysis product gas comprising the steps of flowing said gases into a first trap means, retaining said gases in said first trap means, simultaneously liberating pyrolysis product gases previously retained in a second trap means therefrom, flowing said liberated gases to a gas analyzer, analyzing said liberated gases, and periodically changing the flow pattern of said pyrolysis product gases whereby while a portion of said gases are being retained in one of said trap means, another portion of said gases previously retained in the other of said trap means is being liberated and analyzed. Systems for carrying out the method of the invention are also provided.

It is, therefore, a general object of the present invention to provide an improved method and system for analyzing pyrolysis product gases.

A further object of the present invention is the provision of a method and system for pyrolyzing one or more substances in a single and continuous pyrolysis reaction and analyzing a portion of the pyrolysis product gases produced while another portion is being collected during the reaction.

Yet a further object of the present invention is the provision of a method and system for pyrolyzing one or more substances in a single and continuous pyrolysis reaction and collecting and analyzing the pyrolysis product gases produced in two or more separate portions.

Other and further features, objects and advantages of the invention will be apparent to those skilled in the art upon a reading of the description of preferred embodiments which follows when taken in conjunction with the accompanying drawings.

DESCRIPTION OF THE PREFERRED EMBODIMENTS

Figure 1:
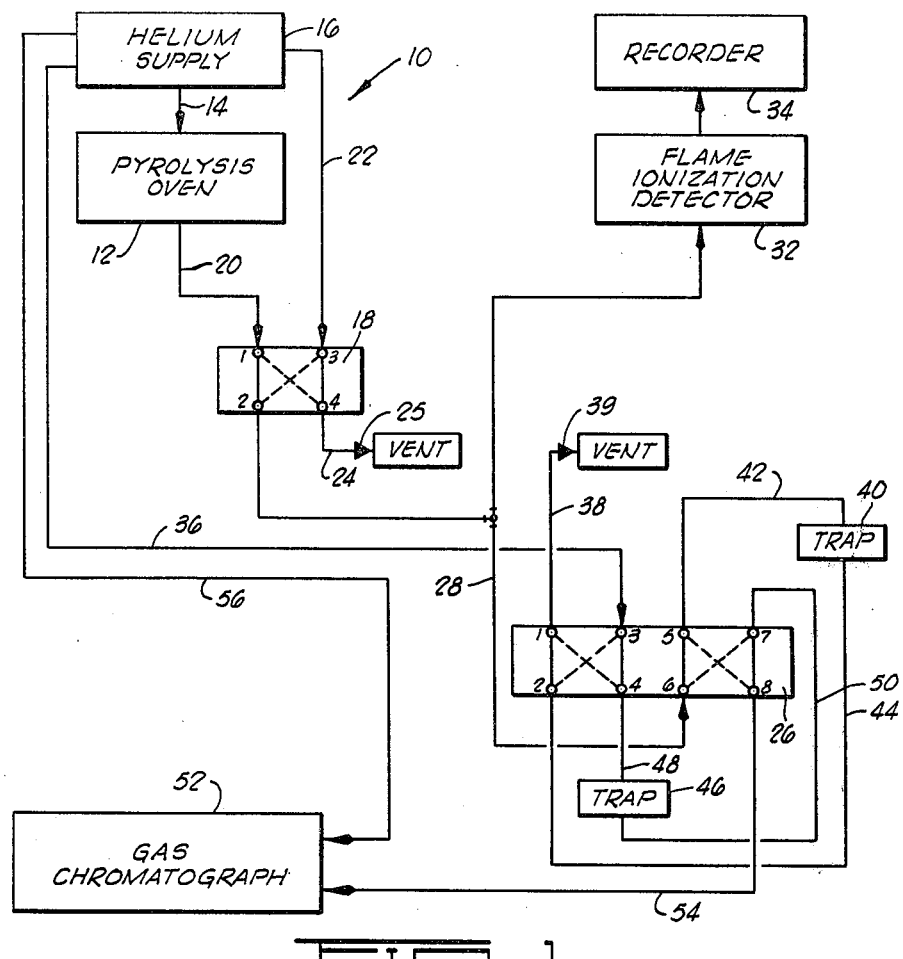
FIG. 1 is a diagrammatic illustration of a system of the present invention for producing and analyzing pyrolysis product gases.

Referring now to the drawings, and particularly to FIG. 1, a system of the present invention is illustrated and generally designated by the numeral 10.

The system 10 is comprised of a conventional pyrolysis oven or furnace 12 wherein a compound or substance such as a core sample can be heated to a desired temperature or at increasing temperatures over a desired period of time. The oven 12 includes a sealable access door, an inert gas inlet connection and a pyrolysis product gas inert gas mixture outlet connection. A conduit 14 is connected to a source of inert gas, preferably helium, and to the inert gas inlet connection of the oven 12. As will be understood, appropriate flow controllers (not shown) are utilized to cause the various streams of helium utilized in the system 10 to flow at desired flow rates.

A conventional two-position four-port valve 18 is provided having four ports designated by numerals 1 through 4. In one operating position, the ports 1 and 3 are communicated with the ports 2 and 4, respectively, as shown by the solid lines on the drawing. In another operating position, the ports 1 and 3 of the four-port valve 18 are communicated with the ports 4 and 2, respectively, as shown by the dashed lines on the drawing. A conduit 20 is connected between the pyrolysis product gas-inert gas outlet connection of the oven 12 and port 1 of the four-port valve 18. A conduit 22 connects the source of helium 16 to port 3 of the valve 18, and a conduit 24 connects the port 4 of the valve 18 to a flow controller 25 and vent. Flow controller 25 functions as a down stream restriction to regulate flow rate.

Two additional two-position four-port valves can be provided, or most preferably, and as shown in the drawing, a single two-position eight-port valve 26 is provided. The eight-port valve 26 includes eight ports marked with the numerals 1 through 8 on the drawing. In one position of the valve 26, the ports 1, 3, 5 and 7 are communicated with the ports 2, 4, 6 and 8, respectively, as shown by the solid lines, and in the other position the ports 1, 3, 5 and 7 are communicated with the ports 4, 2, 8 and 6, respectively, as shown by the dashed lines. As will be readily understood by those skilled in the art, a variety of valve arrangements other than two four-port valves or one eight-port valve can be utilized, including combinations of two-port, three-port, four-port and other types of valves. However, as indicated above, a single eight-port valve is preferred for convenience of operation.

A conduit 28 is connected between port 2 of the four-port valve 18 and port 6 of the eight-port valve 26. A conduit 30 is connected between a connection in the conduit 28 and the inlet connection of a conventional flame ionization detector 32. The detector 32 includes a recorder 34 operably connected therewith for recording the presence of ions detected by the detector 32 on a time chart. A conduit 36 is connected between port 3 of the eight-port valve 26 and the source of helium 16, and a conduit 38 is connected between port 1 of the eight-port valve 26 and a flow controller 39 and a vent. Flow controller 39 serves to regulate flowrates through the traps.

A first pyrolysis product gases trap 40 is provided which is connected to port 5 of the eight-port valve 26 by a conduit 42 and to port 2 of the eight-port valve 26 by a conduit 44. A second pyrolysis product gases trap 46 is connected to port 4 of the eight-port valve 26 by a conduit 48 and to port 7 thereof by a conduit 50.

A conventional gas analyzer 52, preferably a gas chromatograph such as a Hewlett-Packard Model 5730 A is provided, the gas to be analyzed inlet connection of which is connected to port 8 of the eight-port valve 26 by a conduit 54. An inert gas inlet connection on the analyzer 52 is connected by a conduit 56 to the source of inert gas 16.

Figure 2:
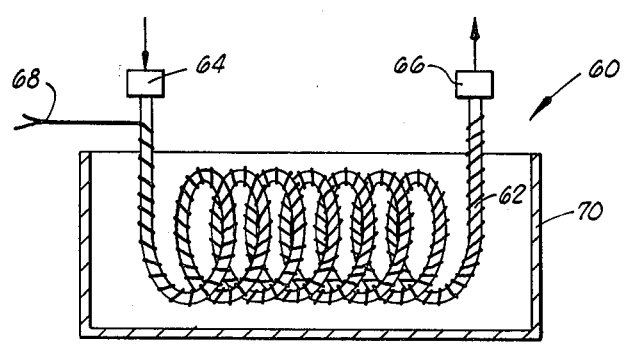
FIG. 2 illustrates one form of a pyrolysis product gases trap which can be utilized in accordance with the invention.

Referring now to FIG. 2, one form of pyrolysis product gases trap which can be utilized as the traps 40 and 46 of FIG. 1 is illustrated and generally designated by the numeral 60. As will be understood, the traps 40 and 46 can be identical or different and can take a variety of forms and designs. As will be described further hereinbelow, the traps function to collect and retain pyrolysis product gases for a period of time followed by the liberation of the retained gases for analysis. In whatever form, the traps 40 and 46 separate the pyrolysis product gases from inert gas in admixture therewith and retain the separated pyrolysis gases either in condensed liquid form or by adsorbing the gases or both. Preferably, the traps 40 and 46 in the system 10 are identical and are in the form of the trap 60 illustrated in FIG. 2. As shown in FIG. 2, the trap 60 is comprised of an elongated U-tube type of tubular enclosure 62 formed into a coiled configuration and including connections 64 and 66 at opposite ends thereof. Conventional heating wire 68 is wrapped around the tube 62 for selectively heating the tube 62 and its contents. A container 70 is positioned around the coiled portion of the tube which can be filled with liquid nitrogen or other coolant whereby the tube 62 is submerged in the coolant and is cooled at desired times. Other heating and cooling means can be utilized which will readily suggest themselves to those skilled in the art. The tube 62 is filled with a packing material (not shown) for providing a substrate upon which pyrolysis product gases are condensed when the tube 62 is cooled. Preferably, the packing material is an adsorbent having an affinity for at least the low molecular weight compounds contained in the pyrolysis product gases generated in the system 10 whereby such compounds are adsorbed by the solid adsorbent material. Three angstrom molecular sieves are particularly preferred for use as the packing material within the tube 62.

OPERATION OF THE SYSTEM 10

In operation of the system 10 for carrying out the method of the present invention, a substance to be pyrolyzed is placed in the pyrolysis oven 12 and heated to a desired, substantially constant temperature or in a manner whereby the temperature of the substance is increased over a period of time. Streams of inert gas are caused to flow at selected flow rates through the pyrolysis oven 12 by way of the conduit 14, to the eight-port valve 26 by way of the conduit 36 and to the analyzer 52 by way of the conduit 56. Pyrolysis product gases produced in the oven 12 are carried by the inert gas carrier through the conduit 20 to the four-port valve 18. The four-port valve 18 is positioned whereby the pyrolysis product gas-inert gas mixture flows through the valve 18 by way of communicated ports 1 and 2 thereof and into the conduit 28. The eight-port valve 26 is positioned whereby ports 1, 3, 5 and 7 are communicated with ports 2, 4, 6 and 8 thereof, respectively. The gases flowing to the eight-port valve 26 by way of the conduit 28 flow through the valve 26 by way of communicated ports 5 and 6, through the conduit 42 and into the trap 40. The trap 40 is cooled whereby as the pyrolysis product gas-inert gas mixture flows through the trap 40, at least a portion of the pyrolysis product gases are condensed and caused to accumulate within the trap 40 whereby they are separated from the inert gas carrier. Uncondensed pyrolysis product gases are adsorbed on the packing material contained within the trap 40 whereby they are also separated from the inert gas and the residual inert gas flows by way of the conduit 44, the communicated ports 1 and 2 of the eight-port valve 26 and the conduit 38 to a vent. The stream of inert gas flowing through the conduit 36 flows through the communicated ports 3 and 4 of the eight-port valve 26 and the conduit 48 into the trap 46. The trap 46 is heated while the inert gas stream is flowing therethrough whereby condensed pyrolysis product liquids contained within the trap 46 are vaporized and pyrolysis product gases adsorbed on the packing material disposed within the trap 46 are desorbed therefrom. The thus liberated pyrolysis product gases from the trap 46 flow by way of the conduit 50, through the communicated ports 7 and 8 of the valve 26 and through the conduit 54 into the analyzer 52 where the pyrolysis product gases are analyzed. Thus, while pyrolysis product gases are being retained in the trap 40, pyrolysis gases previously retained in the trap 46 are simultaneously liberated therefrom and analyzed.

After a desired period of time or when the substance within the oven 12 is heated to a selected temperature or temperature range, the position of the eight-port valve 26 is changed whereby ports 1, 3, 5 and 7 are communicated with ports 4, 2, 8 and 6, respectively. This causes the pyrolysis product gas-inert gas mixture flowing to the eight-port valve 26 by way of the conduit 28 to flow through the communicated ports 6 and 7 thereof, through the conduit 50 and into the trap 46. The trap 46 is cooled while the valve 26 is in such position whereby pyrolysis product gases are retained therein in the manner described above in connection with the trap 40. Residue inert gas flows out of the trap 46 by way of the conduit 48, the communicated ports 1 and 4 of the valve 26 and into the conduit 38 from where it is conducted to a vent. The stream of inert gas flowing to the valve 26 by way of the conduit 36 flows into the conduit 44 by way of the communicated ports 2 and 3 of the valve 26 and from the conduit 44 into the trap 40 which is heated whereby pyrolysis product gases retained in the trap 40 are liberated in the same manner as described above in connection with the trap 46. The liberated pyrolysis product gases flow by way of the conduit 42 through the communicated ports 5 and 8 of the valve 26 and into the conduit 54 which leads the gases to the analyzer 52 where they are analyzed.

During the operation of the pyrolysis oven 12, a small stream of the pyrolysis product gas-inert gas mixture is caused to flow from the conduit 28 by way of the conduit 32 to the flame ionization detector 32. The detector 32 detects the presence of ions in the gas mixture thereby indicating the start, duration and termination of the pyrolysis reaction taking place within the oven 12, which information is recorded on the recorder 34.

As will now be apparent, when the position of the eight-port valve 26 is changed during the pyrolysis of a substance in the oven 12, the flow pattern of the pyrolysis product gas-inert gas mixture flowing from the oven is changed whereby the gas mixture is caused to flow through the trap 40 or 46 from which retained pyrolysis product gases were just liberated, and gases in the trap 40 and 46 which have just been collected and retained are simultaneously liberated therefrom and analyzed. Thus, while the pyrolysis reaction is being carried out in a single continuous step, two or more separate samples of the pyrolysis product gases produced can be selectively collected and individually analyzed. In addition, because a portion of the pyrolysis product gases produced is being analyzed while the pyrolysis reaction is proceeding, the system 10 and method carried out thereby are more efficient and require less time for analyzing pyrolysis product gases than prior systems and methods.

When it is desired to vent the gases produced in the oven 12 and purge the remaining portions of the system 10 with inert gas, the position of the four-port valve 18 is changed whereby the gases from the oven 12 flow through the conduit 20, through the communicated ports 1 and 4 of the valve 18 and to the vent by way of the conduit 24. Simultaneously, the inert gas stream flowing through the conduit 22 flows through the valve 18 by way of the communicated ports 2 and 3 thereof and into the conduit 28 whereby it flows through the rest of the system as described above.

Thus, the present invention is well adapted to carry out the objects and attain the ends and advantages mentioned as well as those inherent therein. While numerous changes in the sequence of steps as well as the arrangement and construction of the various parts of the present invention will suggest themselves to those skilled in the art, such changes are encompassed within the spirit of this invention as defined by the appended claims.

The embodiments of the invention in which an exclusive property or privilege is claimed are defined as follows:

1. A system for subjecting one or more materials to pyrolysis and for trapping and analyzing the product gases therefrom comprising:

a pyrolysis oven having an inert gas inlet connection and a product gas outlet connection;

a means defining a source of inert gas;

a first conduit connected between said means defining a source of inert gas and said inert gas inlet connection of said oven;

a two-position four-port valve including first, second, third and fourth ports whereby in one position said first and third ports are communicated with said second and fourth ports, respectively, and in the other position, said first and third ports are communicated with said fourth and second ports, respectively;

a second conduit connected between said product gas outlet of said oven and said first port of said four-port valve;

a third conduit connected between said means defining a source of inert gas and said third port of said four-port valve;

a two-position eight-port valve having first, second, third, fourth, fifth, sixth, seventh and eighth ports whereby in one position said first, third, fifth and seventh ports are communicated with said second, fourth, sixth and eighth ports, respectively, and in the other position, said first, third, fifth and seventh ports are communicated with said fourth, second, eighth and sixth ports, respectively;

a fourth conduit connected between said second port of said four-port valve and said sixth port of said eight-port valve;

a first trap means for condensing, retaining and then vaporizing said pyrolysis product gases having an inlet connection and an outlet connection;

a fifth conduit connected between said fifth port of said eight-port valve and said inlet connection of said first trap means;

a sixth conduit connected between said outlet connection of said first trap means and said second port of said eight-port valve;

a seventh conduit connected between said means defining a source of inert gas and said third port of said eight-way valve;

a second trap means for condensing, retaining and then vaporizing said pyrolysis product gases having an inlet connection and an outlet connection;

an eighth conduit connected between said fourth port of said eight-port valve and said inlet connection of said second trap means;

a ninth conduit connected between said outlet connection of said second trap means and said seventh port of said eight-way valve;

a gas analyzer; and a tenth conduit connected between said gas analyzer and said eighth port of said eight-port valve.

2. The system of claim 1 wherein said first and second trap means are each comprised of:
an elongated tubular enclosure having inlet and outlet connections at opposite ends thereof;
a quantity of pacing material providing a substrate for condensing said pyrolysis product gases and having an affinity for at least light hydrocarbons contained in said gases disposed within said enclosure; and
means for selectively cooling and heating said enclosure attached thereto.

3. The system of claim 2 wherein said material providing a substrate for condensing said pyrolysis product gases and having an affinity for light hydrocarbons is 3 angstrom molecular sieve packing.

4. The system of claim 2 which is further characterized to include an eleventh conduit connected between said first port of said eight-port valve and a vent.

5. The system of claim 4 which is further characterized to include a twelfth conduit connected between said fourth port of said four-port valve and a vent.

6. The system of claim 5 which is further characterized to include a thirteenth conduit connected between said fourth conduit and an ionization detector.

* * * * *

UNITED STATES PATENT OFFICE
CERTIFICATE OF CORRECTION

PATENT NO. : 4,325,907

DATED : April 20, 1982

INVENTOR(S) : Harry Dembicki, Jr., and Roger A. Woods

It is certified that error appears in the above-identified patent and that said Letters Patent are hereby corrected as shown below:

Column 7, line 7, "pacing" should be --packing--.

Signed and Sealed this

Tenth Day of August 1982

[SEAL]

Attest:

GERALD J. MOSSINGHOFF

Attesting Officer

Commissioner of Patents and Trademarks